United States Patent
Sathe et al.

(10) Patent No.: US 10,266,507 B2
(45) Date of Patent: Apr. 23, 2019

(54) PROCESS FOR THE PREPARATION OF RANOLAZINE

(71) Applicant: UNICHEM LABORATORIES LIMITED, Mumbai (IN)

(72) Inventors: Dhananjay G. Sathe, Thane (IN); Dnyaneshwar V. Gawas, Sattari (IN); Sanjay Bhaskar Chowkekar, Mumbai (IN); Jotirling Ramling Mali, Osmanabad (IN)

(73) Assignee: UNICHEM LABORATORIES LIMITED, Mumbai, Maharastra (IN)

( * ) Notice: Subject to any disclaimer, the term of this patent is extended or adjusted under 35 U.S.C. 154(b) by 0 days.

(21) Appl. No.: 15/552,053

(22) PCT Filed: Mar. 4, 2016

(86) PCT No.: PCT/IB2016/051228
§ 371 (c)(1),
(2) Date: Aug. 18, 2017

(87) PCT Pub. No.: WO2016/142819
PCT Pub. Date: Sep. 15, 2016

(65) Prior Publication Data
US 2018/0044307 A1 Feb. 15, 2018

(30) Foreign Application Priority Data
Mar. 10, 2015 (IN) .......................... 766/MUM/2015

(51) Int. Cl.
*C07D 295/15* (2006.01)

(52) U.S. Cl.
CPC ................................. *C07D 295/15* (2013.01)

(58) Field of Classification Search
CPC ..................................................... C07D 295/15
See application file for complete search history.

(56) References Cited

U.S. PATENT DOCUMENTS

2011/0151258 A1* 6/2011 Anumula et al. ......... B32B 5/16
428/402

* cited by examiner

*Primary Examiner* — Erich A Leeser
(74) *Attorney, Agent, or Firm* — Bacon & Thomas, PLLC

(57) ABSTRACT

A process for the preparation of Ranolazine (I) and its acid addition salts and the process for the preparation of compound of formula (7).

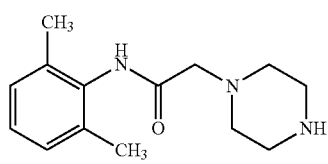

(7)

7 Claims, No Drawings

PROCESS FOR THE PREPARATION OF RANOLAZINE

PRIORITY

This application claims the benefit of IN766/MUM/2015, filed on Mar. 10, 2015, the content of which is incorporated herein by reference.

TECHNICAL FILED

The present invention relates to novel processes for the preparation of Ranolazine (I) and its acid addition salts.

BACKGROUND OF THE INVENTION

Ranolazine is marketed under the brand name Ranexa® and is indicated for the treatment of chronic angina. Ranexa may be used with beta-blockers, nitrates, calcium channel blockers, anti-platelet therapy, lipid-lowering therapy, ACE inhibitors, and angiotensin receptor blockers. Ranolazine is a racemic mixture, chemically described as 1-piperazineacetamide, N-(2,6-dimethylphenyl)-4-[2-hydroxy-3-(2-methoxyphenoxy) propyl]-, (±)-indicated by compound of formula (1).

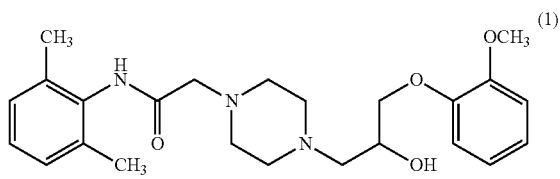 [SMILES: COc1ccccc1OCC(O)CN1CCN(CC(=O)Nc2c(C)cccc2C)CC1]

U.S. Pat. No. 4,567,264 teaches two methods for the preparation process of Ranolazine.

Method 1 disclosed reaction of 2-methoxyphenol compound of formula (2) with epichlorohydrin in presence of water, dioxane and NaOH to obtain 1-(2-methoxyphenoxy)-2,3-epoxypropane compound of formula (3) which is condensed with piperazine in presence of ethanol to obtain 2-(2-methoxyphenoxy)-1-(piperazin-1-yl) ethanol compound of formula (4). Reacting 2,6-Dimethylaniline compound of formula (5) with chloroacetyl chloride in presence of TEA and MDC to obtain 2-chloro-N-(2,6-dimethylphenyl) acetamide compound of formula (6). Compound of formula (4) was condensed with compound of formula (6) in presence of dimethylformamide to obtain Ranolazine compound of formula (1). The method (1) is depicted below as scheme (I).

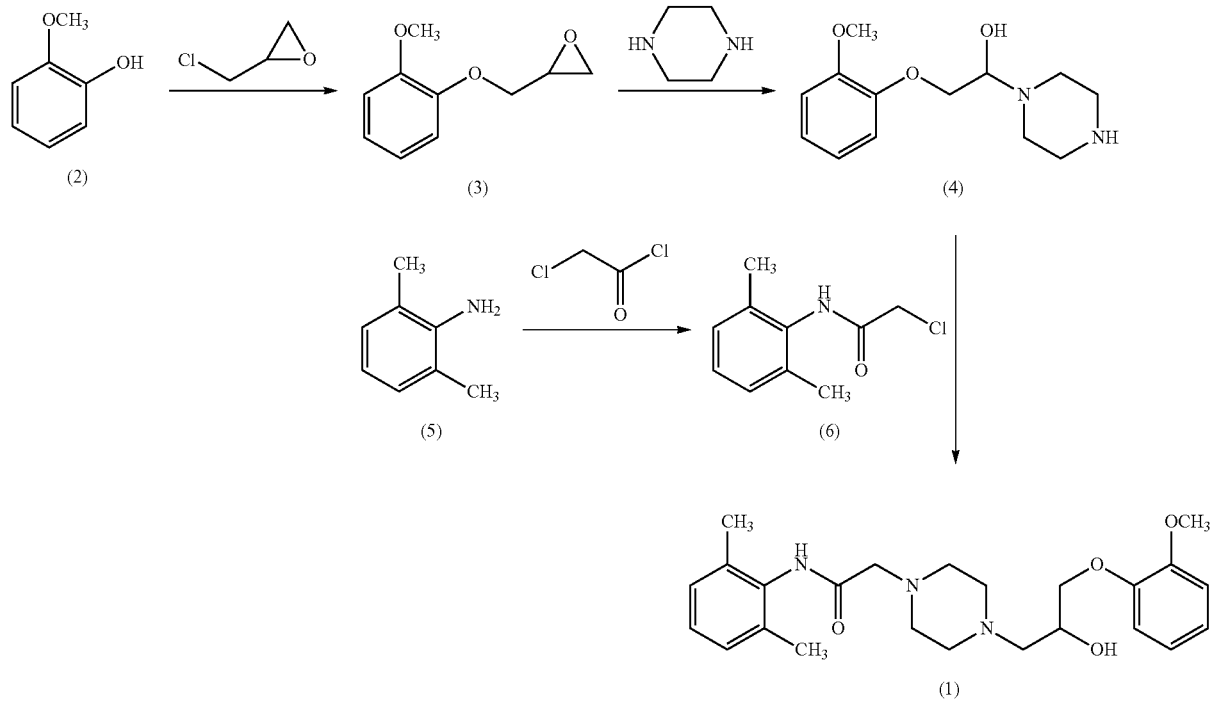

US'264 taught another method for preparation of Ranolazine by condensing compound of formula (6) with piperazine in presence of ethanol to obtain N-(2,6-dimethylphenyl)-2-(piperazin-1-yl) acetamide compound of formula (7). Compound of formula (3) was condensed with compound of formula (7) in presence of mixture of methanol and toluene at reflux temperature. The obtained Ranolazine is purified by column chromatography on silica gel. Excess of hydrochloric acid in methanol was added to get dihydrochloride salt of Ranolazine which was converted into its free base by suspending it in ether and stirred with excess of dilute aqueous potassium carbonate to get Ranolazine free base. The scheme is depicted below by Scheme (II).

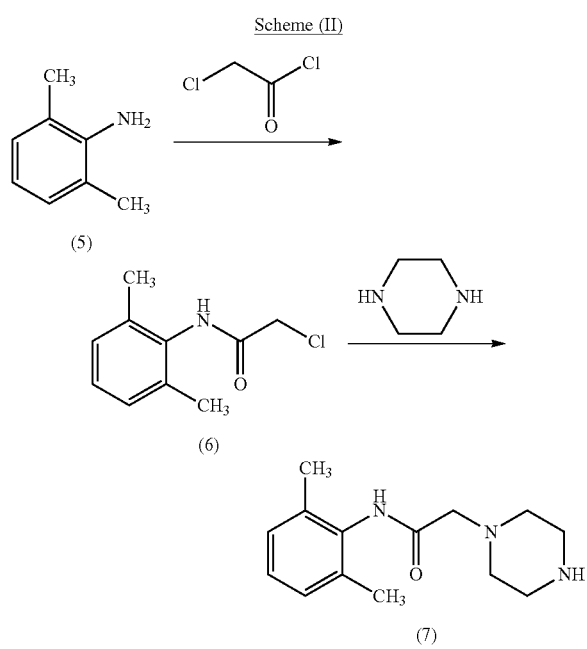

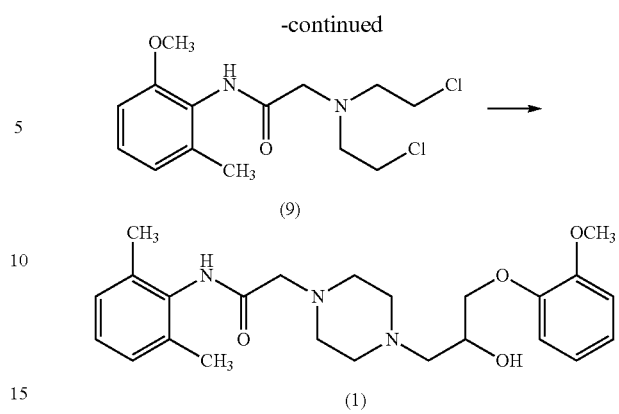

Chinese patent application No. 102875490 disclosed condensation of compound of formula (6) with N-Boc-piperazine to obtain compound of formula (10) in the presence of $K_2CO_3$ in EtOH, removal of Boc group by means of TFA in EtOAc gives compound of formula (7) which is then converted into Ranolazine. The synthetic scheme is depicted below in scheme (IV).

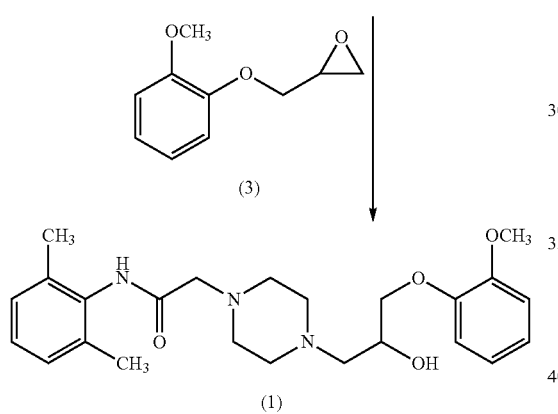

EP0483932A1 disclosed condensation of condensation of N, N-bis(2-chloroethyl)-amino]-2,6-dimethyl acetanilide compound of formula (9) with 1-[3-(2-methoxyphenoxy)-2-hydroxy]propylamine compound of formula (8) to obtain Ranolazine base. The base was purified by column chromatography; hydrochloride salt was formed by treating with methanolic HCl. The detailed impurity profile study was not reported for Ranolazine. The synthetic scheme is depicted below in scheme (III).

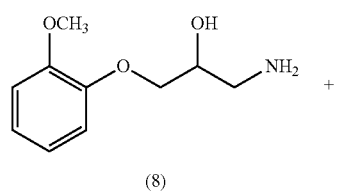

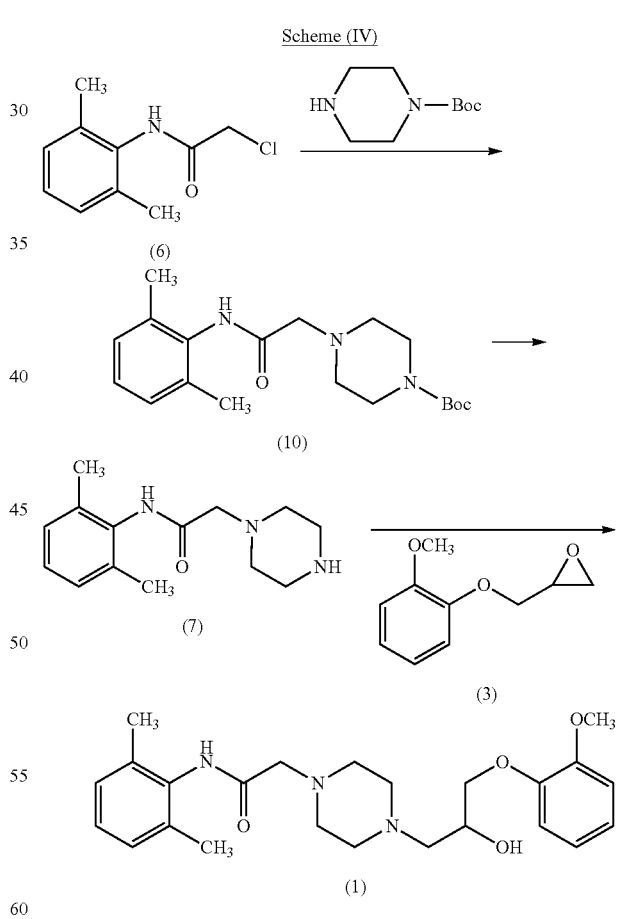

Organic Process Research & Development 2012, 16, 748-754 disclosed condensation of compound of formula (6) with piperazine in methanol to produce compound of formula (7), in which unwanted solid bis alkylated compound of formula (11) was filtered. The resulting filtrate pH adjusted to 5.0-5.5 with 44% phosphoric acid solution to recover piperazine monophosphate monohydrate salt. The compound of formula (7) was extracted with MDC. PCT application No. 2008/047388 disclosed a process for the preparation Ranolazine, by reacting 2,6-dimethyl aniline with Chloroacetyl chloride in the presence of base in water. The resulting amide intermediate is reacted with piperazine, and the resulting piperazine derivative is further condensed with 1-(2-methoxyphenoxy)-2,3-epoxypropane in an inert solvent to produce crude Ranolazine, which is further purified by crystallizing from organic solvents selected from alcohols or aromatic hydrocarbons. Ranolazine obtained in the disclosed art does not have satisfactory purity for pharmaceutical use. Unacceptable amounts of impurities are generally formed along with Ranolazine. In addition, the processes involve the additional step of column chromatographic purifications, which are generally undesirable for large-scale operations.

As described above the cited literature processes suffer from many drawbacks like use of excess amount of piperazine during the reaction, which is difficult to handle in large scale; generation of large amount of effluent due to excessive use of piperazine, that is difficult to recover and recycle; Ranolazine obtained as an oil is difficult to handle in large scale production and laborious chromatographic techniques are used for purification of Ranolazine.

It is observed that pharmaceutically acceptable salts of Ranolazine when prepared from impure Ranolazine do not meet the pharmaceutical acceptable quality. There is therefore, an unfulfilled need to provide industrially feasible process for the preparation of Ranolazine free base and its acid addition salt with high purity. The present invention provides Ranolazine of high purity by using phosphate salt of piperazine to prepare Ranolazine. In this process, excess of unreacted piperazine is easy to recover and recycle in the next reactions. Thus it is easy to avoid the generation of large amount of effluent due to reuse of piperazine, which are generally desirable for large-scale operations thereby making the process commercially feasible.

All the available literature uses unprotected piperazine and protected piperazine leading to formation of dimer impurities which are difficult to remove from the product and also resulting in poor overall yield of the product. The maximum daily dosage of Ranolazine is 2 g; therefore, known and unknown impurities must be controlled below 0.05% in the final drug substance.

From the above known fact our main target is:
1. To study the detailed impurity profile to and to control the formation of all the impurities below the desired limit (NMT 0.05%).
2. To obtained the Cost effective process by utilizing the maximum consumption of piperazine in the form of piperazine monophosphate salt there by reducing formation of unwanted impurities and also reusing recovered piperazine.

All the available literature uses unprotected piperazine and protected piperazine leading to formation of dimer impurities which are difficult to remove from the product and also resulting in poor overall yield of the product.

OBJECT OF THE INVENTION

The main object of the present invention is to provide novel process for the preparation of Ranolazine and its acid addition salts.

Another object of the present invention is to provide novel process for the preparation of Ranolazine intermediate compound of formula (7).

Yet another object of the present invention is to control the formation of dimer impurity of [2,6-dimethylphenyl)-aminocarbonylmethyl]chloride compound of formula (11) during the preparation of compound of formula (7).

Yet another object of the present invention is to reuse the unreacted piperazine monophosphate monohydrate in the next reactions, thereby making the process cost effective.

SUMMARY OF THE INVENTION

The present invention provides process for preparing Ranolazine compound of formula (1) or a pharmaceutically acceptable salt thereof comprising the steps of;
a) preparing acid salt of piperazine by adjusting pH of the aqueous solution of piperazine at 4-7 with acid;
b) optionally isolating acid salt of piperazine;
c) reacting acid salt of piperazine with compound of formula (6) to obtain compound of formula (7);
d) optionally isolating compound of formula (7);
e) reacting compound of formula (7) with compound of formula (3) in organic solvent to obtain Ranolazine;
f) optionally converting Ranolazine into its salt.

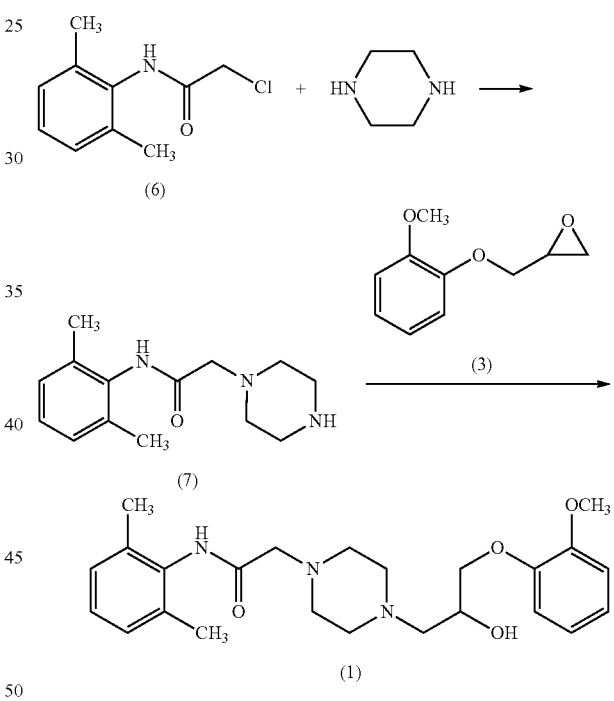

According to another object of the present invention there is provided a novel process for the preparation of Ranolazine intermediate compound of formula (7) comprising steps of;
a) preparing acid salt of piperazine by adjusting pH of the aqueous solution of piperazine at 4-7 with acid;
b) optionally isolating acid salt of piperazine;
c) reacting acid salt of piperazine with compound of formula (6);
d) adjusting pH at 4-7 with base;
e) filtering the unreacted piperazine as a acid salt;
f) adjusting pH of the filtrate to more than 7 with base;
g) extracting compound of formula (7).

According to another object of the present invention, there is provided a novel process for the preparation of Ranolazine intermediate compound of formula (7) comprising steps of;

a) preparing piperazine phosphate salt by adjusting pH of the aqueous solution of piperazine at 4-7 with phosphoric acid;
b) optionally isolating piperazine phosphate salt;
c) reacting piperazine phosphate salt with compound of formula (6);
d) adjusting pH at 4-7 with base;
e) filtering the unreacted piperazine phosphate salt;
f) adjusting pH of the filtrate to more than 7 with base;
g) extracting compound of formula (7).

According to another object of the present invention, there is provided a novel process for the preparation Ranolazine compound of formula (1) or a pharmaceutically acceptable salt thereof comprising the steps of;
a) reacting 2,6-Dimethyl aniline with chloroacetyl chloride in the presence of acetone and aqueous base to give [(2,6-dimethylphenyl)-amino carbonyl methyl]chloride compound of formula (6);
b) reacting sodium salt of Guaiacol with epichlorohydrine to provide 1-(2-methoxyphenoxy)-2,3-epoxypropane compound of formula (3);
c) preparing piperazine phosphate salt by adjusting pH of the aqueous solution of piperazine at 4-7 with phosphoric acid;
d) optionally isolating piperazine phosphate salt;
e) reacting piperazine phosphate salt with compound of formula (6) obtained in step (a) to obtain compound of formula (7);
f) optionally isolating compound of formula (7);
g) reacting compound of formula (7) in organic solvent with compound of formula (3) obtained step (b) to obtain Ranolazine;
h) optionally converting Ranolazine into its salt.

According to another object of the present invention, there is provided a novel process for the preparation Ranolazine compound of formula (1) or a pharmaceutically acceptable salt thereof comprising the steps of;
a) reacting acid salt of piperazine with compound of formula (6) to obtain compound of formula (7);
b) optionally isolating compound of formula (7);
c) reacting compound of formula (7) with compound of formula (3) in organic solvent to obtain Ranolazine;
d) optionally converting Ranolazine into its salt.

According to another object of the present invention, there is provided a process in which recovered acid salt of piperazine is reused or can be reused and is reacted again with compound of formula (6) to obtain compound of formula (7).

DETAILED DESCRIPTION OF THE INVENTION

The present invention relates to an efficient, industrially advantageous and economical process for the preparation of Ranolazine intermediate and subsequently Ranolazine of formula (1) and its acid addition salts thereof.

The present invention also relates to an improved process for preparing pure Ranolazine having purity more than or equal to 99.8%. Present invention eliminates the use of column chromatography, multiple crystallization processes, and tedious, slow filtration operations, so as to get the final product.

The present invention provides novel process for preparing Ranolazine compound of formula (1) or a pharmaceutically acceptable salt thereof comprising the steps of;
a) preparing acid salt of piperazine by adjusting pH of the aqueous solution of piperazine at 4-7 with acid;
b) optionally isolating acid salt of piperazine;
c) reacting acid salt of piperazine with compound of formula (6) to obtain compound of formula (7);
d) optionally isolating compound of formula (7);
e) reacting compound of formula (7) with compound of formula (3) in organic solvent to obtain Ranolazine;
f) optionally converting Ranolazine into its salt.

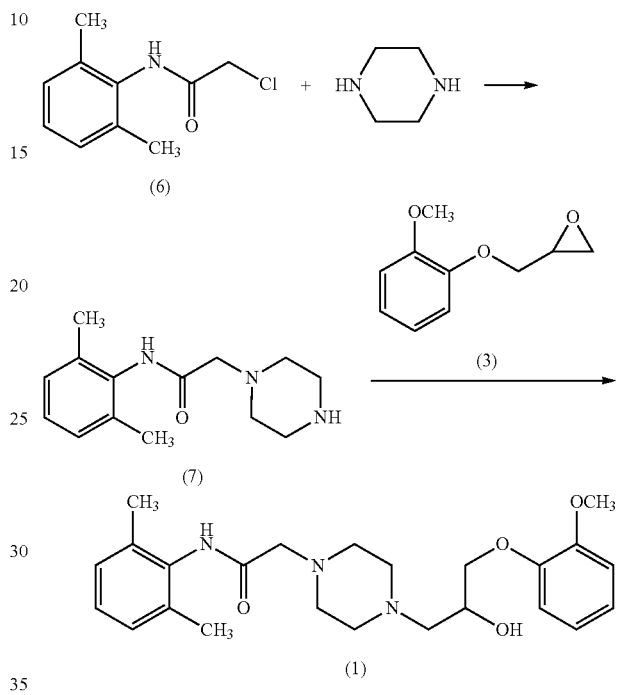

According to present invention acid salt of piperazine is prepared by dissolving piperazine in water and adjusting pH at 4-7, more preferably 5.0-5.5 with acid at temperature range at 25-30° and stirring the reaction mass for about 10-30 minutes.

The example of acid use for the preparation of acid salt of piperazine may include but not limited to formic acid, acetic acid, benzoic acid, p-toluenesulphonic acid, methanesulphonic acid, phosphoric acid, pyrrophosphoric acid, polyphosphoric acid and sulphuric acid.

The term used herein "acid salt of piperazine" refers to piperazine formic acid, acetic acid, benzoic acid, p-toluenesulphonic acid, methanesulphonic acid, phosphoric acid, pyrrophosphoric acid, polyphosphoric acid and sulphuric acid or hydrates of these such as monohydrate, dihydrate, trihydrate, more preferably piperazine monophosphate monohydrate.

The acid salt of piperazine prepared can be isolated or used without isolation in the next reaction step.

The isolation of acid salt of piperazine can be carried out by simple filtration process.

The acid salt of piperazine is reacted with compound of formula (6) at reflux temperature for 6-10 hours and pH of reaction mixture is adjusted at 4-7 using base. Unreacted acid salt of piperazine which is water insoluble is filtered off. Filtrate contains water soluble acid salt of compound of formula (7). The filtrate pH is adjusted to more than 7 with base to obtain free base of compound of formula (7) and can be isolated or used without isolation in the next step of the reaction.

The isolation of compound of formula (7) is carried out in organic solvent such as toluene, ethyl acetate, methylene dichloride, EDC, CHCl$_3$, and CCl$_4$, n-butanol or mixture(s) thereof.

The example of base used for pH adjustment may include but not limited to triethylamine, tributylamine, N, N-diisopropylethylamine, sodium hydroxide, lithium hydroxide, potassium hydroxide, cesium hydroxide, Lithium carbonate, sodium carbonate, potassium carbonate, magnesium carbonate, calcium carbonate, barium carbonate, lithium bicarbonate, sodium bicarbonate, potassium bicarbonate, magnesium bicarbonate, calcium bicarbonate and aqueous solution thereof.

The compound of formula (7) is reacted with compound of formula (3) in presence of organic solvent at a temperature less than about 150° C. or less than about 100° C. to obtain Ranolazine compound of formula (1). The crude product is further isolated by adding water to reaction mass and filtered at cold conditions. The Ranolazine base can be further converted to Ranolazine dihydrochloride by reacting Ranolazine base with HCl.

The example of organic solvent may include but not limited polar solvents such as water, acetone, DMF, DMSO, Actonitrile, Dimethyl acetamide, aliphatic alcohols such as methanol, ethanol, isopropanol, n-propanol, n-butanol, isobutanol, tert-butanol and mixture(s) thereof, more preferably methanol.

Recovered acid salt of piperazine can be further reused and reacted again with compound of formula (6) to obtain compound of formula (7). Again acid salt of piperazine can be recovered with or without addition of Piperazine.

According to another object of the present invention, there is provided a novel process for the preparation of Ranolazine intermediate compound of formula (7) comprising steps of;
a) preparing acid salt of piperazine by adjusting pH of the aqueous solution of piperazine at 4-7 with acid;
b) optionally isolating acid salt of piperazine;
c) reacting acid salt of piperazine with compound of formula (6);
d) adjusting pH at 4-7 with base;
e) filtering the unreacted piperazine as a acid salt;
f) adjusting pH of the filtrate to more than 7 with base;
g) extracting compound of formula (7).

The process for the preparation if acid salt of piperazine and compound of formula (7) is same as described in above.

According to another object of the present invention, there is provided a novel process for the preparation of Ranolazine intermediate compound of formula (7) comprising steps of;
a) preparing piperazine phosphate salt by adjusting pH of the aqueous solution of piperazine at 4-7 with phosphoric acid;
b) optionally isolating piperazine phosphate salt;
c) reacting piperazine phosphate salt with compound of formula (6);
d) adjusting pH at 4-7 with base;
e) filtering the unreacted piperazine phosphate salt;
f) adjusting pH of the filtrate to more than 7 with base;
g) extracting compound of formula (7).

The process according to the present invention, piperazine phosphate salt is refers as monophosphate monohydrate salt.

Piperazine phosphate salt is prepared by dissolving piperazine in water and adjusting pH at 4-7, more preferably 5.0-5.5 with phosphoric acid at temperature range at 25-30° and stirring the reaction mass for about 10-30 minutes.

The Piperazine phosphate salt is reacted with compound of formula (6) at reflux temperature for 6-10 hours and pH of reaction mixture is adjusted at 4-7 using base. Unreacted Piperazine phosphate salt which is water insoluble is filtered off. Filtrate contains water soluble phosphate salt of compound of formula (7). The filtrate pH is adjusted to more than 7 with base to obtain free base of compound of formula (7).

The compound of formula (7) obtained according to the present invention is substantially free from piperazine.

The term used herein "substantially free" refers to the compound of formula (7) having piperazine less than 5% and more preferably less than 1%.

The term used herein "Piperazine phosphate salt" refers to Piperazine monophosphate, diphosphate, pyrophosphate, polyphosphate or hydrate of these such as monohydrate, dihydrate, trihydrate.

According to another object of the present invention there is provided a novel process for the preparation Ranolazine compound of formula (1) or a pharmaceutically acceptable salt thereof comprising the steps of;
a) reacting 2,6-Dimethyl aniline with chloroacetyl chloride in the presence of acetone and aqueous base to give [(2,6-dimethylphenyl)-amino carbonyl methyl]chloride compound of formula (6);
b) reacting sodium salt of Guaiacol with epichlorohydrine to provide 1-(2-methoxyphenoxy)-2,3-epoxypropane compound of formula (3);
c) preparing piperazine phosphate salt by adjusting pH of the aqueous solution of piperazine at 4-7 with phosphoric acid;
d) optionally isolating piperazine phosphate salt;
e) reacting piperazine phosphate salt with compound of formula (6) obtained in step (a) to obtain compound of formula (7);
f) optionally isolating compound of formula (7);
g) reacting compound of formula (7) in organic solvent with compound of formula (3) obtained in step (b) to obtain Ranolazine;
h) optionally converting Ranolazine into its salt.

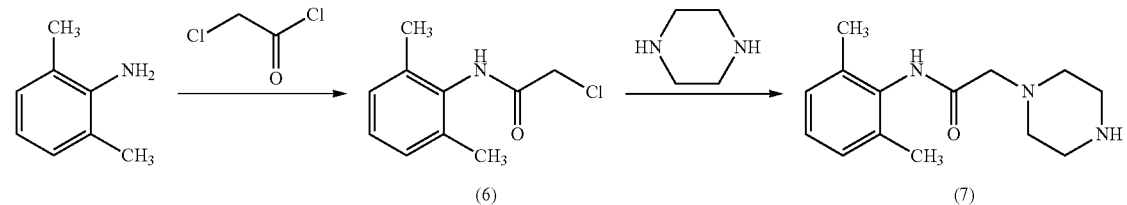

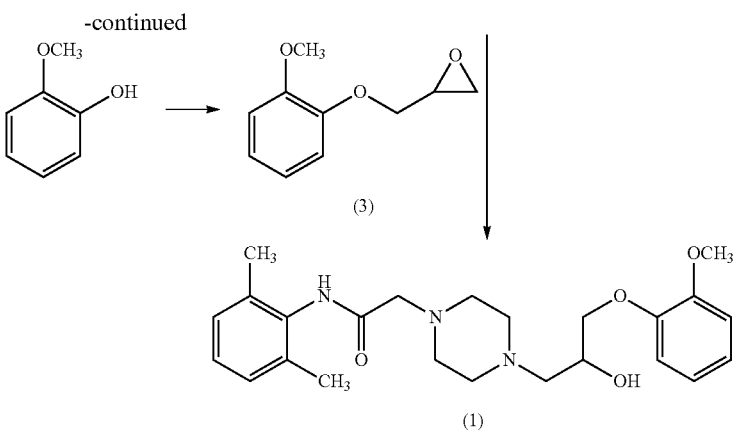

The compound of formula (3) can be isolated as a pure solid in solvent. The example of solvent may include but not limited methanol, ethanol, isopropanol, n-propanol, n-butanol, isobutanol, tert-butanol more preferably isopropanol.

The isolation of compound of formula (6) can be carried out in presence of excess of water and the crude product obtained can be used in the next step with purification.

The reaction conditions are same as described above for reaction of Piperazine phosphate salt with compound of formula (6) to obtain compound of formula (7) which is reacted with compound of formula (3) to obtain Ranolazine.

According to another object of the present invention, there is provided a novel process for the preparation Ranolazine compound of formula (1) or a pharmaceutically acceptable salt thereof comprising the steps of;
 a) reacting acid salt of piperazine with compound of formula (6) to obtain compound of formula (7);
 b) optionally isolating compound of formula (7);
 c) reacting compound of formula (7) with compound of formula (3) in organic solvent to obtain Ranolazine;
 d) optionally converting Ranolazine into its salt.

The reaction condition for the preparation of compound of formula (7) and its reaction with compound of formula (3) to conversion into the Ranolazine are described as earlier.

The invention also comprises process for preparation of compound of formula (7) free from bis-alkylated impurity having compound of formula (11). The bis-alkylated impurity is formed during the reaction of compound of formula (6) with acid salt of piperazine. This bis-alkylated impurity is removed by simple filtration process along with piperazine phosphate salt.

Prior art processes are associated with formation of impurities (12) and (13) to a great extent and their removal is a typical problem in prior art. Surprisingly in the present invention it was noticed that these impurities i.e. (12) and (13) are present in surprisingly low amounts giving a purer yield. The process also provides an advantage of reusing piperazine monophosphate monohydrate and thereby reduces the cost of production.

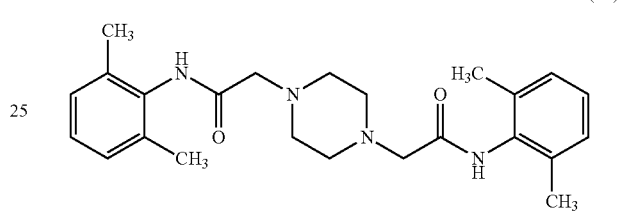

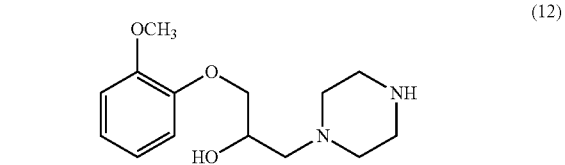

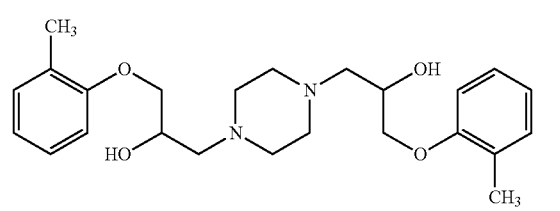

EXAMPLES

The following examples are presented for illustration only, and are not intended to limit the scope of the invention or appended claims.

Example 1

Preparation of [(2,6-Dimethylphenyl)-amino carbonyl methyl) chloride (6)

To 0.74 kg of potassium carbonate and 2.51 ml of water, was added. 500 gm of 2,6-Dimethyl aniline in 1.25 L of Acetone at 0-5° C. 650 gm of Chloroacetyl chloride was added to the reaction mixture below 5° C. and stirred for 3 hrs. 2500 ml of water was added, stirred for 1 hr, filtered the product, washed with water and dried at 75° C. to get [(2,6-Dimethylphenyl)-amino carbonyl methyl]chloride (6). Yield: 95%; purity >98%

Example 2

Preparation of 1-(2-Methoxy phenoxy)-2,3-epoxy propane (3)

Added 2.5 L of water to R.B Flask, 80 gms of NaOH was added and stirred to dissolve. Added 500 gms of Guaiacol, 1.12 Kg of Epichlorohydrine and stirred at 25-350 C for 5-6 h. The organic layer was separated. To the Epichlorohydrine layer charged 160 gms NaOH dissolved in 2.5 L of water and stirred at 25-30° C. for 3-4 h. The organic layer was separated and washed with 150 gms NaOH dissolved in 1.5 L of water. Excess Epichlorohydrine was recovered by distillation of the product layer at 90° C. under vacuum (600-700 mmHg) to give 650-680 gms of oil. To the crude oil was added 3.0 L of Isopropanol and cooled to 0° C. and filtered the product to get 1-(2-Methoxy phenoxy)-2,3-epoxy propane (3).

Yield: 80%; purity >98%.

Example 3

Preparation of Piperazine Monophosphate Monohydrate

Added 1000 ml of water to R.B Flask 109 gms piperazine was added and stirred to dissolve. pH was adjusted to 5.0-5.5 with O-phosphoric acid. After stirring for 1-2-h at room temperature. Filtered the reaction mass and solid was isolated as piperazine monophosphate monohydrate.

Example 4

Preparation of Compound of Formula (7)

Added 1000 ml of water to R.B Flask. 109 gms piperazine was added and stirred to dissolve. pH was adjusted to 5.0-5.5 with O-phosphoric acid. After stirring for 1-2-h at room temperature. Filtered the reaction mass and solid was isolated as piperazine monophosphate monohydrate and charged further to R.B Flask containing 1000 ml water. 100 gms of [(2,6-Dimethylphenyl)-amino carbonyl methyl)chloride (6) was added and heated the reaction mixture at reflux temperature for 7-8 h. Cooled the reaction mixture at 25-30° C. and adjusted the pH to 5.5-6.0 with dilute sodium hydroxide solution filtered. Filtrate was washed with 100 ml×2 methylene chloride and further basified with dilute sodium hydroxide solution and extracted with 500 ml×3 methylene chloride to obtained compound of formula (7).

Example 5

Preparation of Ranolazine

Added 1000 ml of water to R.B Flask 109 gms piperazine was added and stirred to dissolve. pH was adjusted to 5.0-5.5 with O-phosphoric acid, 100 gms of [(2,6-Dimethylphenyl)-amino carbonyl methyl)chloride (6) was added and heated the reaction mixture at reflux temperature for 7-8 h. Cooled the reaction mixture at 25-30° C. and adjusted pH to 5.5-6.0 with dilute sodium hydroxide solution and filtered. Filtrate was washed with 100 ml×2 methylene chloride and further basified with dilute sodium hydroxide solution and extracted with 500 ml×3 methylene chloride. Combined organic layer was washed with saturated brine solution and 80 gm of 1-(2-Methoxy phenoxy)-2,3-epoxy propane (3) was added. Distilled out Methylene chloride under reduced pressure, added 500 ml methanol and refluxed for 5-6 h. Cooled the reaction mass to room temperature and added 500 ml water and cooled to 0° C. Filtered the product to get crude Ranolazine. Yield: 80%; purity >99%.

Example 6

Preparation of Ranolazine from Recovered Piperazine Monophosphate Monohydrate Added 1000 ml of water to R.B Flask 109 gms piperazine was added and stirred to dissolve. Added recovered piperazine monophosphate monohydrate and pH was adjusted to 5.0-5.5 with O-phosphoric acid, 100 gms of [(2,6-Dimethylphenyl)-amino carbonyl methyl)chloride (6) was added and heated the reaction mixture at reflux temperature for 7-8 h. Cooled the reaction mixture at 25-30° C. and adjusted pH 5.5-6.0 with dilute sodium hydroxide solution and filtered. Filtrate was washed with 100 ml×2 methylene chloride and further basified with dilute sodium hydroxide solution and extracted with 500 ml×3 methylene chloride. Combined organic layer was washed with saturated brine solution and 80 gm of 1-(2-Methoxy phenoxy)-2,3-epoxy propane (3) was added. Distilled out Methylene chloride under reduced pressure, added 500 ml methanol and refluxed for 5-6 h. Cooled the reaction mass to room temperature and added 500 ml water and cooled to 0° C. Filtered the product to get crude Ranolazine. Yield: 80%; purity >99%.

Example 7

Preparation of Ranolazine

Added 1000 ml of water to R.B Flask 109 gms piperazine was added and stirred to dissolve. pH was adjusted to 5.0-5.5 with O-phosphoric acid. 100 gms of [(2,6-Dimethylphenyl)-amino carbonyl methyl)chloride (6) was added and heated the reaction mixture at reflux temperature for 7-8 h. Cooled the reaction mixture at 25-30° C., adjusted pH to 5.5-6.0 with dilute sodium hydroxide solution and filtered. Filtrate was washed with 100 ml×2 methylene chloride and further basified with dilute sodium hydroxide solution and extracted with 500 ml×3 methylene chloride. Combined organic layer was washed with saturated brine solution and 80 gm of 1-(2-Methoxy phenoxy)-2,3-epoxy propane (3) was added. Distilled out Methylene chloride under reduced pressure, added 500 ml isopropyl alcohol, refluxed for 5-6 h. cooled the reaction mass to 0° C. Filtered the product to get crude Ranolazine. Yield: 80%; purity >98%.

Example 8

Preparation of Ranolazine

Added 1000 ml of water to R.B Flask 109 gms piperazine was added and stirred to dissolve. pH was adjusted to 5.0-5.5 with O-phosphoric acid. After stirring for 1-2-h at room temperature. Filtered the reaction mass and solid was isolated as piperazine monophosphate monohydrate and charged further to R.B Flask containing 1000 ml water. 100 gms of [(2,6-Dimethylphenyl)-amino carbonyl methyl)chloride (6) was added and heated the reaction mixture at reflux temperature for 7-8 h. Cooled the reaction mixture at 25-30° C. and adjusted the pH to 5.5-6.0 with dilute sodium hydroxide solution filtered. Filtrate was washed with 100 ml×2 methylene chloride and further basified with dilute sodium hydroxide solution and extracted with 500 ml×3 methylene chloride. Combined organic layer was washed with saturated brine solution and 80 gm of 1-(2-Methoxy phenoxy)-2,3-epoxy propane (3) was added. Distilled out Methylene chloride under reduced pressure, added 500 ml methanol and refluxed for 5-6 h. Cooled the reaction mass to room temperature, added 500 ml water, cooled to 0° C. and filtered the product to get crude Ranolazine. Yield: 80%; purity >99%.

Example 9

Purification of Ranolazine

Added 300 ml of methanol to R.B Flask, 100 gms of crude ranolazine piperazine and heated to dissolve. Added Activated charcoal and filtered the hot solution through hyflo and washed the hyflo with 100 ml methanol. Reaction mixture was cooled to room temperature. 200 ml water was added and was cooled further to 0-5° C. Filtered to afford pure Ranolazine. Yield: 90%; purity >99.9%.

We claim:

1. A process for preparing Ranolazine compound of formula (1) or a pharmaceutically acceptable salt thereof comprising the steps of;
   a) preparing an acid salt of piperazine by adjusting pH of an aqueous solution of piperazine at 4-7 with an acid;
   b) optionally isolating the acid salt of piperazine;
   c) reacting the acid salt of piperazine with a compound of formula (6) to obtain a compound of formula (7);
   d) optionally isolating the compound of formula (7);
   e) reacting the compound of formula (7) with a compound of formula (3) in a solvent to obtain Ranolazine compound of formula (1);
   f) optionally converting Ranolazine compound of formula (1) into its salt

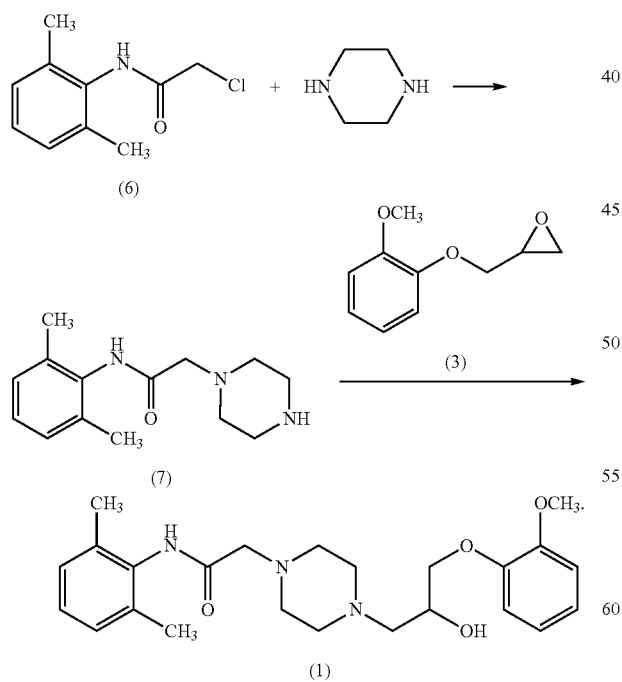

2. The process according to claim 1, wherein the acid is selected from the group consisting of formic acid, acetic acid, benzoic acid, p-toluenesulphonic acid, methanesulphonic acid, phosphoric acid, pyrrophosphoric acid, polyphosphoric acid and sulphuric acid.

3. The process according to claim 1, wherein the acid salt of piperazine is a phosphate salt.

4. The process according to claim 1, wherein the solvent is selected from the group consisting of water, acetone, DMF, DMSO, Acetonitrile, Dimethyl acetamide, methanol, ethanol, isopropanol, n-propanol, n-butanol, isobutanol, tert-butanol and mixture(s) thereof.

5. A process for preparing Ranolazine compound of formula (1)

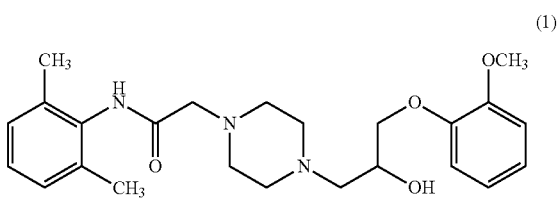 [SMILES: COc1ccccc1OCC(O)CN1CCN(CC(=O)Nc2c(C)cccc2C)CC1]

or a pharmaceutically acceptable salt thereof comprising the steps of;

reacting an acid salt of piperazine with a compound of formula (6)

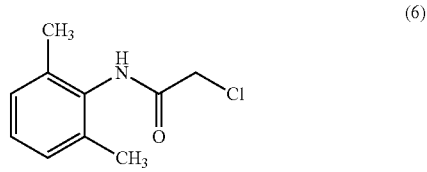

to a obtain compound of formula (7);

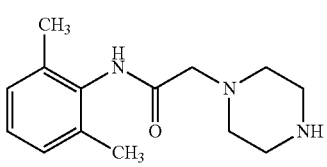

optionally isolating the compound of formula (7);

reacting compound of formula (7) with compound of formula (3) in a solvent to obtain Ranolazine compound of formula (1);

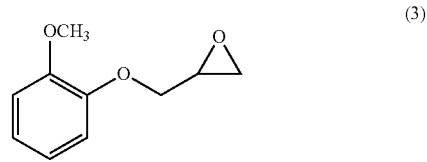 [SMILES: COc1ccccc1OCC1CO1]

optionally converting Ranolazine compound of formula (1) into its salt.

6. The process according to claim 5, wherein the acid salt of piperazine is a phosphate salt.

7. The process according to claim 5, wherein the solvent is selected from group consisting of water, acetone, DMF, DMSO, Acetonitrile, Dimethyl acetamide, aliphatic alcohols such as methanol, ethanol, isopropanol, n-propanol, n-butanol, isobutanol, tert-butanol and mixture(s) thereof.

* * * * *